United States Patent [19]

Knopp et al.

[11] Patent Number: 4,930,354

[45] Date of Patent: Jun. 5, 1990

[54] AUTOMATIC BOND DETERMINATOR

[75] Inventors: Leslie C. Knopp, Neenah; Kenneth M. Baumgartle, Appleton, both of Wis.

[73] Assignee: Hartley Controls Corporation, Neenah, Wis.

[21] Appl. No.: 318,862

[22] Filed: Mar. 6, 1989

[51] Int. Cl.⁵ ............................................. G01N 11/00
[52] U.S. Cl. ...................................................... 73/823
[58] Field of Search .................... 73/821, 823; 364/502

[56] References Cited

U.S. PATENT DOCUMENTS

| | | | |
|---|---|---|---|
| 2,647,397 | 8/1953 | Dietert | 73/821 X |
| 2,791,120 | 5/1957 | Dietert | 73/821 X |
| 3,050,992 | 8/1962 | Steinmueller et al. | 73/795 |
| 3,054,286 | 9/1962 | Karol | 73/825 X |
| 3,353,407 | 11/1967 | Dietert et al. | 73/765 |
| 3,638,478 | 2/1972 | Dietert et al. | 73/823 X |
| 4,569,025 | 2/1986 | Eirich et al. | 366/132 X |
| 4,616,508 | 10/1986 | Jörn | 73/823 |

Primary Examiner—Jerry W. Myracle
Attorney, Agent, or Firm—Wheeler Law Firm

[57] ABSTRACT

A device for testing the quality of foundry green sand is described including a delivery structure with an invertible riddle, a testing structure with a compaction plunger, and sensors for measuring the compaction and moisture content of the sample, another testing structure with a sensor for measuring the green compressive strength of the sample, and a specimen tube mounted on carriage which traverses between delivery and testing structures. A strike off device levels the sample within the specimen tube. The floor of the specimen tube can be raised to eject the sample after testing and the same strike off device cleans the raised floor. A control panel activates and coordinates the operation of the device. A data processor analyzes the information yielded by the testing apparatus and automatically initiates the correct addition of any additives as needed.

4 Claims, 3 Drawing Sheets

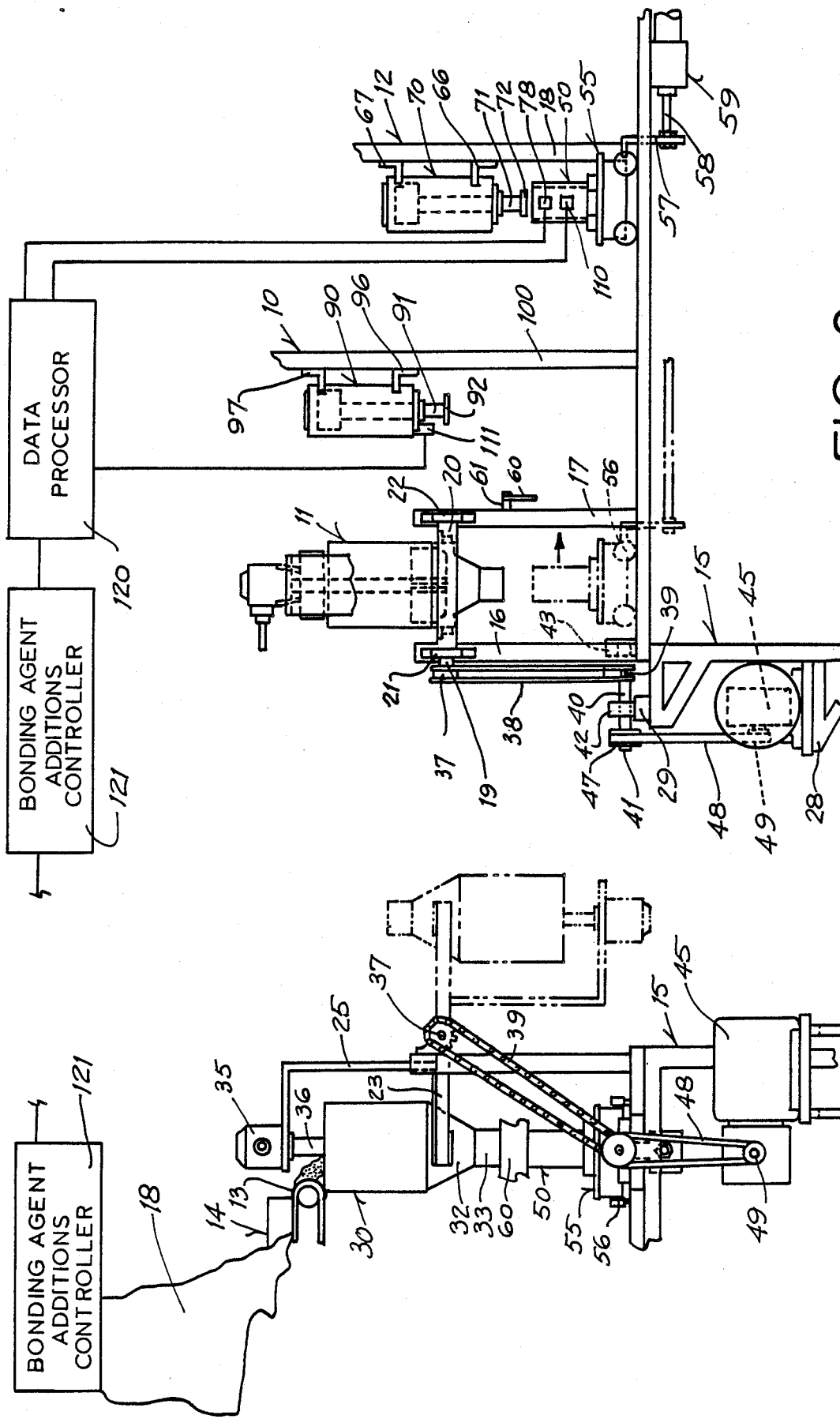

AUTOMATIC BOND DETERMINATOR

BACKGROUND OF THE INVENTION

This invention is a further development of the invention of U.S. Pat. No. 4,699,011.

The idea of the invention is to provide a fuller and more comprehensive device to automate sand testing more fully.

The known references further include Dietert U.S. Pat. No. 2,647,397, which shows merely a standard tube test done without automatic features. Dietert U.S. Pat. No. 2,791,120 shows some features, such as a thermocouple to measure sand temperature, but added water is "measured" by a timer. Permeability is measured but all measurements are merely displayed rather than automatically determining and activating the necessary response of the equipment. U.S. Pat. No. 3,050,992 to Steinmueller et al is merely a tester to measure sand strength in multiple ways. It does not alter the sand as a result. Dietert U.S. Pat. No. 3,353,407 is a test apparatus and a sand conditioner, but the structure, mechanical function and method of using the data recorded are all different from the present invention. Dietert U.S. Pat. No. 3,638,478 shows an integrated tester which adjusts the additive dispensing structure, but which is mechanically different from this device. Jorn U.S. Pat. No. 4,616,508 shows very generalized test apparatus to control additives to foundry sand. Karol U.S. Pat. No. 3,054,276 is a soil tester and doesn't condition anything.

SUMMARY OF THE INVENTION

The device of this invention is an automatic bond determinator. The invention functions by testing a sample from a bath of foundry green sand. The amount of bonding agent present in the sample is determined. The data is then compared to the desired bond level to initiate the necessary changes to achieve the optimum bond level in the sand for use in foundry green sand.

The invention functions as follows:

Sand is automatically fed in to a specimen tube through a riddle. The specimen tube is filled with the foundry green sand until it overflows the top of the specimen tube. The specimen tube is mounted on a platform capable of moving in a horizontal direction. When the specimen tube is full the platform begins to move toward the first testing station of the automatic determinator. As the tube moves towards the first testing station it passes under a strike off device that is positioned to strike off any excess sand on top of the tube. This assures the reliability of each test run since the amount of sand placed in the tube will always be of the same volume. The specimen tube moves toward the first testing station where it stops under a plunger. The plunger is capable of moving into and out of the specimen tube. After the specimen tube stops in position underneath the plunger, the plunger then goes into the specimen tube compressing the sand in the tube under a specific pressure. The degree of compaction of the sand at that specific pressure is then measured by a sensor and sent to a data processor where the data is held until the other tests are completed. After the sand has been compacted a second test is performed at the first testing station. The percent moisture within the sand is determined by measuring the electrical conductivity of the sand. This measurement is also sent to the data processor.

After the above two tests have been completed, the platform on which the specimen tube is mounted automatically proceeds to the second testing station. The bottom floor of the specimen tube is capable of moving in an upward or downward manner. Once the specimen tube arrives at the second testing station the bottom floor of the specimen tube extrudes exactly two inches of the compacted specimen. These two inches are extruded directly under a second plunger that has a flat self-aligning surface. This second plunger is not capable of entering into the specimen tube. The second plunger presses down onto the compacted specimen of extruded sand until the point at which the compacted specimen compresses to the point of fracture. The force required to do this is measured and then sent to the data processor.

Once the force needed to fracture the free standing sand column has been determined, the second piston or plunger retracts to its normal position and the specimen tube begins to travel back towards the riddle where it can receive another sample. The sand that is within the specimen tube is ejected by raising the bottom floor of the specimen tube to the top of the specimen tube and passing the specimen tube back under the strike off device which removes any sand that remains on the top of the specimen tube and the bottom floor. The bottom floor of the specimen tube then lowers back down to its original position and the specimen tube is ready to receive another sample.

The three pieces of information determined by the tests performed by the automatic bond determinator are placed into a formula by the data processor which determines the changes necessary to achieve the optimum bond level. If a change is required, the data processor will automatically change the level of bond additive by sending a signal to the bond additive adding device.

DESCRIPTION OF THE DRAWINGS

FIG. 1 is an end view of the automatic bond determinator of the present invention showing the delivery structure thereof and also schematically showing the riddle in its inverted position.

FIG. 2 is a side view of the present invention.

DETAILED DESCRIPTION

Figure 3:
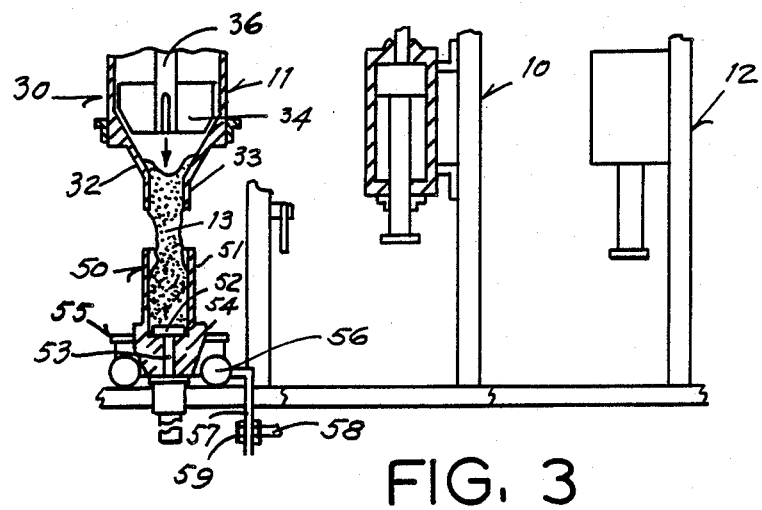
FIG. 3 is a side view of a portion of the present invention with parts out away showing the carriage located under the delivery structure.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The automatic bond determinator includes a delivery structure 11 and two testing structures 12 and 10 both supported by a frame 15. Sand 13, from sand supply 18, is brought by a conveyor belt system 14 to the delivery structure 11 (see FIG. 2) which is intended to deliver the sand 13 loose and uncompacted to the specimen tube 50.

As seen in FIGS. 1 and 2, the delivery structure 11 is primarily supported by vertical supports 16 and 17 which are mounted to the frame 15. Shaft 20 is joined to bearing blocks 21 and 22 which are mounted on vertical supports 16 and 17, respectively. End 19 of shaft 20 extends beyond bearing block 21 and sprocket 37 is mounted thereon. Horizontal supports 23 and 24 [not shown] and bracket 25 are mounted on shaft 20. A riddle 30 is mounted between horizontal supports 23 and 24 and the agitator motor 35 is mounted on bracket 25, with agitator shaft 36 extending downward through bracket 25 and into the riddle 30.

Shaft 40 is joined through bearing block 43 which is mounted on the frame 15 and through bearing block 42 which is mounted on bracket 29 which in turn is mounted on the frame 15. End 41 of the shaft 40 extends the bracket 29 and pulley 47 is mounted thereon. Sprocket 39 is also mounted on shaft 40 and is linked to sprocket 37 by chain 38. Bracket 28 which is mounted on the frame 15 supports motor 45 which turns pulley 49. Pulley 49 is connected to pulley 47 by belt 48.

Referring to FIG. 1 the delivery structure 11 operates as follows: A pre-determined amount of sand 13, enough to overflow the specimen tube 50, is brought by the conveyor belt system 14 and cascades into the riddle 30 where it comes to rest on a screen 31 having a desirable mesh located in the generally conical shape funnel portion 32 of the riddle 30. The sand 13 is sifted when fins 34, in the riddle 30, on agitator shaft 36 work the sand 13 through the screen 31. The riddled sand 13 falls through the cylindrical spout portion 33 of the riddle 30 and into the spout 33 directly below. The spout 33 has a diameter smaller than that of the standard 2" diameter specimen tube 50 to insure that little sand 13 is spilled, and is located sufficiently below the riddle 30 to insure that the sand 13 is loose and uncompacted when it falls into the specimen tube 50.

When motor 45 is activated, horizontal supports 23 and 24 rotate 180 degrees around shaft 20, inverting the riddle 30 (see FIG. 1) and emptying it of any remaining sand which did not pass through screen 31. Compressed air jets (not shown) may be added to aid the removal of such particles. When motor 45 is activated in reverse, the riddle 30 returns to its original portion and is ready to deliver another sample.

Referring to FIG. 3, the specimen tube 50 has cylindrical walls 51 and a plate-like movable floor 52 which fits slideably within the walls 51. The floor 52 of specimen tube 50 can be raised or lowered by rods 53 which extend out of and retract into tube 54. The specimen tube 50 is mounted on a carriage 55 and a tube 54 extends downwardly therefrom.

Figure 4:
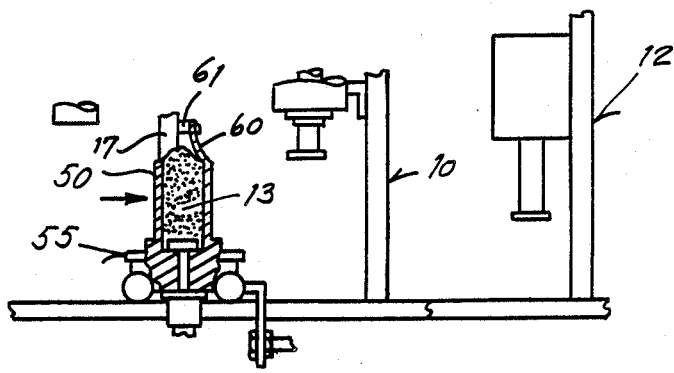
FIG. 4 is a side view of the present invention with parts out away showing the operation of the strike off device.

Rod 58, which extends out of and retracts into tube 59, is fixedly attached to bracket 57 with its mounted on the carriage 55. The wheels 56 of the carriage 55 ride on horizontal rails 26 and 27 (not shown) which are mounted on the frame 15 and separated to accommodate tube 54 which extends downwardly form the carriage 55. The carriage 55 and hence the specimen tube to 50 can, therefore, traverse from under the riddle 30 on the delivery structure 11 to its correct position on testing structure 12 and vice-versa, as shown in FIG. 1. While in transit, a strike off device 60, which is mounted by post 61 to support 17 so as to pass over the top of the specimen tube 50, levels the sand 13 therein (see FIG. 4). Hereinafter, the sand 13 in the specimen tube 50 will be referred to as the "specimen" but still, however, denoted by the numeral 13.

Figure 5:
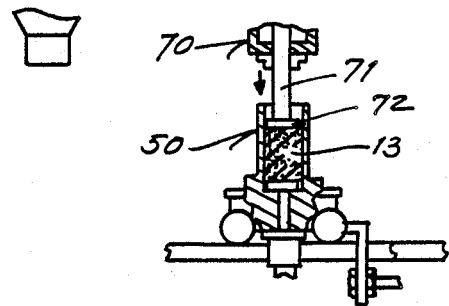
FIG. 5 is a side view with parts cut away showing the carriage under the testing structures with the compaction plunger inserted into the specimen tube.

The test structures 10 and 12 are primarily supported by supports 100 and 18 respectively, which are mounted to the frame 15. The squeeze tube 70 is mounted to support 18 by brackets 66 and 67. The squeeze tube 90 is mounted to support 100 by brackets 97 and 96. Rod 71 which extends downwardly out of and retracts into the squeeze tube 70, has a flat ended plunger 72 of a size equal to that of the floor 52 of the specimen tube 50. Rod 91, which extends downwardly out of and retracts into the squeeze tube 90, has a plate-like plunger 92 of a size greater than that of the floor 52 of the specimen tube 50. The test structure 12 operates as follows:

As seen in FIGS. 5 and 1, when the specimen tube 50 is correctly positioned under the squeeze tube 70, rod 71 extends downwardly and plunger 72 uniformly compresses the specimen 13 until a pre-determined pressure is achieved and maintained for a pre-determined length of time. This pressure is recorded as the compactability of the specimen 13 by the linear digital transducer 78 that is contained within tube 50. As the compactability is determined by the linear digital transducer 78 another sensor 110 contained within the tube 50 tests the moisture content of the specimen 13 by measuring the electrical conductance through the specimen 13. The information, moisture content and compactability is then sent to the data processor 120 and held for future integration.

Once these measurements are taken, rod 71 retracts into the squeeze tube 70 thereby withdrawing the plunger 72 from the specimen tube 50. The specimen tube 50 then begins to move back toward the test structure 10.

Figure 6:
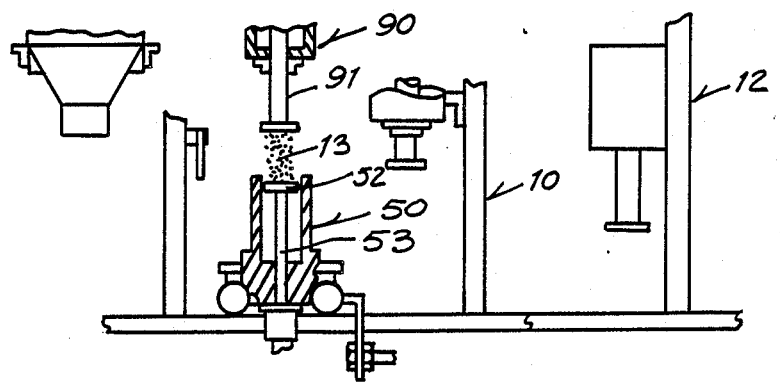
FIG. 6 is a side view showing the present invention measuring the green compressive strength of the specimen.

The test structure 10 operates as follows:

As seen in FIG. 6, when the specimen tube 50 is correctly positioned under the squeeze tube 90, the floor 53 of the specimen tube 50 is raised by rod 52 which extrudes a portion of the specimen 13 out of the specimen tube 50. Rod 91 then extends downwardly and plunger 92 uniformly and steadily increases pressure compressing the specimen 13 until it fractures. The point at which the specimen 13 fractures is the maximum measured force and is translated into a green compressive strength, this information is then sent to the data processor 120 via sensor 111.

Figure 7:
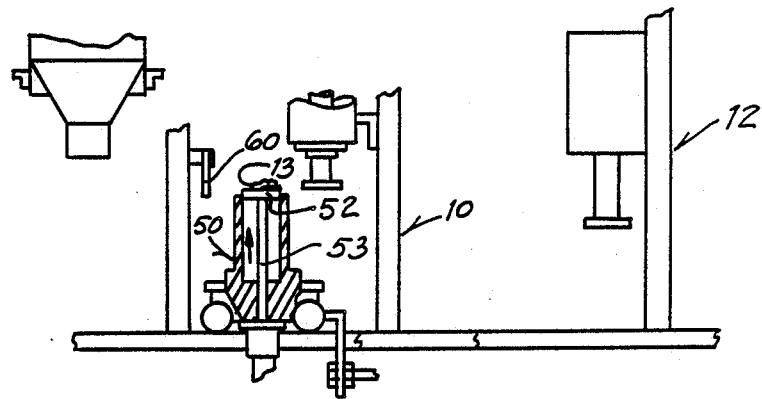
FIG. 7 is a side view of a portion of the present invention with parts cut away showing the bottom of the specimen raised to its ejection position.

Once this measurement is taken, rod 91 retracts into the squeeze tube 90 thereby withdrawing the plunger 92 from contact with the specimen 13. The specimen tube 50 then begins to move toward the delivery structure 11. Before reaching the wiper 60, rod 53 elevates the floor 52 of the specimen tube 50 slightly above the top of the specimen tube 50 as shown, in FIG. 7, and ejects the specimen 13. The strike off device 60 then sweeps across the floor 52 of specimen tube 50 to ensure that the entire specimen 13 is removed. By the time the specimen tube 50 is once again positioned under the riddle 30, the floor 52 is retracted by rod 51 to the bottom of the specimen tube 50.

The compactability, moisture, and green compressive strength measurements that were sent to the data processor 120 are now factored into an industry accepted Formula and the percent available clay content of the sand is determined. There are four variables to the formula; compactibility, moisture, green compressive strength, and percentage of available clay. When any three of the four variables are known, the fourth variable can be calculated. By taking the three tests done by the apparatus (compactibility, moisture, and green compressive strength) and applying the formula, we determine the percentage of available clay to within one hundredth of one percent (0.01%). This information is then entered into another formula in the data processor 120, whereby the amount of clay change required to bring the sand to the desired percent of available clay content is calculated. This information is then automatically used to determine if it is necessary to increase or decrease the level of bonding agents added to the foundry's sand in order to maintain the desired level. When the desired amount of bonding agent has been calculated, the message is sent automatically to the bonding agent addition controller to either increase or decrease the amount of bonding agent to be added.

The above described embodiments of this invention are merely descriptive of its principles and are not to be limiting. The scope of this invention instead shall be determined from the scope of the following claims, including their equivalents.

In the following claims the term green compressive strength shall have the same meaning it had in the above description.

What is claimed is:

1. An automatic bond determinator for measuring the amount of bonding agent in a sample of foundry green sand having mounting means on which is mounted a delivery structure and two testing structures comprising:

a riddle mounted on said delivery structure;
   said riddle including a screen positioned to sift foundry green sand;
   a specimen tube having a first position below said riddle to receive sifted foundry green sand;
   said tube having a vertically movable bottom;
   means for raising and lowering said bottom of said specimen tube to eject foundry green sand from said tube;
   means for leveling foundry green said within said specimen tube;
   means for traversing said specimen tube to a second position at the first said testing structure and then to a third position at the second said testing structure;
   said first testing structure including a compacting plunger and means for moving said plunger in and out of said specimen tube only while mounted on said first testing structure in said second position such that said foundry green sand within said specimen can be uniformly compressed at a specific pressure by said plunger;
   means for measuring and recording said compression of said foundry green sand in said specimen tube;
   said first testing structure also including means for measuring and recording the moisture content of said foundry green sand in said specimen tube;
   after compression said foundry green sand being a compacted specimen;
   said second testing structure including a green compressive strength plunger and means for moving said plunger up and down onto said compacted specimen only while mounted on said second testing structure in said third position such that a predetermined amount of said compacted specimen is extruded from the specimen tube by said raising and lowering means and said extruded compacted specimen is pressed by said green compressive strength plunger until said compacted specimen fractures;
   means for measuring and recording the pressure exerted by the green compressive strength plunger at moment said compacted specimen fractures;
   means for automatically adding water and other additives to the foundry green said system from which said sample of foundry green sand in said specimen tube came;
   means for transferring said measurements and recordings to a means for processing and analyzing each said measurement made at each said testing structure;
   said means for processing and analyzing being capable of determining if said means for automatically changing the quantity of water and other ingredients should be engaged;
   whereby the amount of bonding agent in the sample is determined and if more or less bonding agent is required, the proper amount is added to the foundry green sand system to maintain a desired level.

2. The device of claim 1 in which the means for measuring the moisture content of the foundry green sand is a device that measures the electrical conductance through the compacted foundry green sand.

3. The device of claim 1 in which the green compressive strength is the measure of force against the extruded compacted specimen at the moment said extruded specimen fractures.

4. The device of claim 1 in which the means for processing and analyzing each said measurement is a programmable controller or computer whereby the information it receives may be factored into any formula desired.

* * * * *